United States Patent
Sieli et al.

(10) Patent No.: US 9,452,955 B2
(45) Date of Patent: Sep. 27, 2016

(54) PROCESS FOR PRODUCING DISTILLATE FUELS AND ANODE GRADE COKE FROM VACUUM RESID

(71) Applicant: Lummus Technology Inc., Bloomfield, NJ (US)

(72) Inventors: Gary Sieli, Sayreville, NJ (US); Ahmad Faegh, Missouri City, TX (US); Ujjal K. Mukherjee, Montclair, NJ (US); Mario C. Baldassari, Morris Plains, NJ (US); Marvin I. Greene, Clifton, NJ (US)

(73) Assignee: Lummus Technology Inc., Bloomfield, NJ (US)

( * ) Notice: Subject to any disclaimer, the term of this patent is extended or adjusted under 35 U.S.C. 154(b) by 266 days.

(21) Appl. No.: 14/184,099

(22) Filed: Feb. 19, 2014

(65) Prior Publication Data

US 2014/0275676 A1 Sep. 18, 2014

Related U.S. Application Data

(60) Provisional application No. 61/784,462, filed on Mar. 14, 2013.

(51) Int. Cl.
  *C10G 69/06* (2006.01)
  *C07C 4/06* (2006.01)
  (Continued)

(52) U.S. Cl.
  CPC ............... *C07C 4/06* (2013.01); *C10G 9/005* (2013.01); *C10G 69/06* (2013.01); *C10G 2300/202* (2013.01)

(58) Field of Classification Search
  CPC ........... C07C 4/00; C07C 4/06; C10G 9/005; C10G 67/00; C10G 67/02; C10G 69/06
  See application file for complete search history.

(56) References Cited

U.S. PATENT DOCUMENTS

| 4,213,846 A | 7/1980 | Sooter et al. |
| 4,443,325 A * | 4/1984 | Chen et al. ............... 208/55 |

(Continued)

FOREIGN PATENT DOCUMENTS

| CN | 1309164 A | 8/2001 |
| CN | 1325938 A | 12/2001 |

(Continued)

OTHER PUBLICATIONS

International Search Report and Written Opinion issued Jun. 2, 2014 in corresponding PCT application No. PCT/US2014/017742 (12 pages).

(Continued)

*Primary Examiner* — Brian McCaig
(74) *Attorney, Agent, or Firm* — Osha-Liang LLP

(57) ABSTRACT

A process for upgrading residuum hydrocarbon feedstocks that may include: contacting a residuum hydrocarbon and hydrogen with a hydroconversion catalyst in a residuum hydroconversion reactor system; recovering an effluent from the residuum hydroconversion reactor system; separating the effluent to recover two or more hydrocarbon fractions including at least a vacuum residuum fraction and a heavy vacuum gas oil fraction; combining at least a portion of the heavy vacuum gas oil fraction and at least a portion of the vacuum residuum fraction to form a mixed heavy hydrocarbon fraction; feeding at least a portion of the mixed heavy hydrocarbon fraction to a coker; operating the coker at conditions to produce anode grade green coke and distillate hydrocarbons; recovering the distillate hydrocarbons from the coker; fractionating the distillate hydrocarbons to recover hydrocarbon fractions including a light distillates fraction, a heavy coker gas oil fraction, and a coker recycle fraction.

33 Claims, 3 Drawing Sheets

(51) Int. Cl.
*C10G 9/00* (2006.01)
*C10G 67/00* (2006.01)
*C10G 67/02* (2006.01)
*C07C 4/00* (2006.01)

(56) References Cited

U.S. PATENT DOCUMENTS

| | | |
|---|---|---|
| 4,676,886 A | 6/1987 | Rahbe et al. |
| 4,882,036 A | 11/1989 | Eidt, Jr. et al. |
| 4,976,848 A | 12/1990 | Johnson |
| 4,990,243 A | 2/1991 | Winslow et al. |
| 5,013,427 A | 5/1991 | Mosby et al. |
| 5,071,805 A | 12/1991 | Winslow et al. |
| 5,177,047 A | 1/1993 | Threlkel |
| 5,215,955 A | 6/1993 | Threlkel |
| 5,277,793 A | 1/1994 | Bezman et al. |
| 5,439,860 A | 8/1995 | Habib et al. |
| 5,472,928 A | 12/1995 | Scheuerman et al. |
| 5,543,036 A * | 8/1996 | Chang et al. ................ 208/189 |
| 5,593,570 A | 1/1997 | Habib et al. |
| 5,925,235 A | 7/1999 | Habib |
| 6,096,190 A | 8/2000 | Cash |
| 6,200,462 B1 | 3/2001 | Cash et al. |
| 6,224,747 B1 | 5/2001 | Cash et al. |
| 6,514,403 B1 | 2/2003 | Louie et al. |
| 6,783,660 B2 | 8/2004 | Dahlberg et al. |
| 6,797,154 B2 | 9/2004 | Mukherjee et al. |
| 8,206,574 B2 | 6/2012 | Etter |
| 2002/0179493 A1 | 12/2002 | Etter |
| 2006/0032788 A1 | 2/2006 | Etter |
| 2009/0314685 A1 | 12/2009 | Soares et al. |
| 2011/0094937 A1 * | 4/2011 | Subramanian et al. ........ 208/40 |
| 2012/0269685 A1 | 10/2012 | Etter |

FOREIGN PATENT DOCUMENTS

| | | |
|---|---|---|
| CN | 1351126 A | 5/2002 |
| WO | 99/64540 A1 | 12/1999 |
| WO | 2008012485 A1 | 1/2008 |

OTHER PUBLICATIONS

"Resid Conversion Options", Reynolds, Roger, Spieler, S., Broussard, R.A.; Chevron Research and Technology, Richmond, California; No. 1998.073, p. 16-26, www.oildrop.org.

Office Action issued in Chinese Application No. 201480021127.X; Dated Apr. 28, 2016 (24 pages).

* cited by examiner

PROCESS FOR PRODUCING DISTILLATE FUELS AND ANODE GRADE COKE FROM VACUUM RESID

CROSS-REFERENCE TO RELATED APPLICATIONS

This application, pursuant to 35 U.S.C. §119(e), claims priority to U.S. Provisional Application Ser. No. 61/784,462, filed Mar. 14, 2013 which is herein incorporated by reference in its entirety.

FIELD OF THE DISCLOSURE

Embodiments disclosed herein relate generally to processes for upgrading vacuum residuum streams derived from petroleum, tar sands, shale oils, coal liquids, coal gasification tars and biocrudes, among others. More particularly, embodiments herein relate to processes for producing distillate fuels and anode grade coke from vacuum residua hydrocarbon feedstocks. Even more particularly, embodiments disclosed herein relate to processes for upgrading vacuum residua feedstocks to distillate fuel products using ebullated bed or slurry hydrocracking, delayed coking, and fixed bed catalytic vacuum gas oil upgrading.

BACKGROUND

Thermal coking processes allow crude oil refineries to process heavier hydrocarbons present in petroleum, tar sands, and other hydrocarbon sources. In general, thermal coking processes employ high-severity, thermal decomposition (or "cracking") to maximize the conversion of very heavy, low-value residuum feeds to lower boiling hydrocarbon products of higher value. Feedstocks for these coking processes normally consist of refinery process streams which cannot economically be further distilled, catalytically cracked, or otherwise processed to make fuel-grade blend streams. Typically, these materials are not suitable for catalytic operations because of catalyst fouling and/or deactivation by ash and metals. Common coking feedstocks include atmospheric distillation residuum, vacuum distillation residuum, catalytic cracker residual oils, hydrocracker residual oils, and residual oils from other refinery units.

Three types of coking processes used in crude oil refineries and upgrading facilities to convert the heavy hydrocarbon fractions into lighter hydrocarbons and petroleum coke include delayed coking, fluid coking, and flexicoking. In all three of these coking processes, the petroleum coke is considered a by-product that is tolerated in the interest of more complete conversion of refinery residues to lighter hydrocarbon compounds. The resulting hydrocarbons and other products move from the coking vessel to a fractionator in vapor form. The heavier cracked liquids (e.g. gas oils) are commonly used as feedstocks for further refinery processing (e.g. Fluid Catalytic Cracking Units or FCCUs) that transforms them into transportation fuel blend stocks.

Crude oil refineries have regularly increased the use of heavier crudes in their crude blends due to greater availability and lower costs. These heavier crudes have a greater proportion of the heavier hydrocarbon components, increasing the need for coker capacity. Thus, the coker often becomes a bottleneck that limits refinery throughput. Also, these heavier crudes often contain higher concentrations of large, aromatic structures (e.g. asphaltenes and resins) that contain greater concentrations of sulfur, nitrogen, and heavy metals, such as vanadium and nickel.

As a result, the coking reactions (or mechanisms) are substantially different and tend to produce a denser, shot (vs. sponge) coke crystalline structure (or morphology) with higher concentrations of undesirable contaminants in the pet coke and coker gas oils. Unfortunately, many of the technology improvements attempting to deal with the above (plant capacity/bottlenecks, feedstock compositional changes, etc.) have substantially decreased the quality of the resulting pet coke. Most of the technology improvements and heavier, sour crudes tend to push the pet coke from porous sponge coke to shot coke with higher concentrations of undesirable impurities. The resulting shift in coke quality can require a major change in coke markets (e.g. anode to fuel grade) and dramatically decrease coke value. The changes in technology and associated feed changes can result in decreased quality of the fuel grade coke, having lower volatile matter and gross heating value, among other properties, making the produced fuel grade coke less desirable.

SUMMARY OF THE CLAIMED EMBODIMENTS

In one aspect, embodiments disclosed herein relate to a process for upgrading residuum hydrocarbon feedstocks. The process may include: contacting a residuum hydrocarbon and hydrogen with a hydroconversion catalyst in an residuum hydroconversion reactor system; recovering an effluent from the residuum hydroconversion reactor system; separating the effluent from the residuum hydroconversion reactor system to recover two or more hydrocarbon fractions including at least a vacuum residuum fraction and a heavy vacuum gas oil fraction; combining at least a portion of the heavy vacuum gas oil fraction and at least a portion of the vacuum residuum fraction to form a mixed heavy hydrocarbon fraction; feeding at least a portion of the mixed heavy hydrocarbon fraction to a coker; operating the coker at conditions to produce anode grade green coke and distillate hydrocarbons; recovering the distillate hydrocarbons from the coker; fractionating the distillate hydrocarbons recovered from the coker to recover three or more hydrocarbon fractions including a light distillates fraction, a heavy coker gas oil fraction, and a coker recycle fraction.

In another aspect, embodiments herein relate to a system for upgrading residuum hydrocarbon feedstocks. The system may include: a residuum hydroconversion reactor system for contacting a residuum hydrocarbon and hydrogen with a hydroconversion catalyst; a fractionation system for separating an effluent recovered from the residuum hydroconversion reactor system into two or more hydrocarbon fractions including at least a vacuum residuum fraction and a heavy vacuum gas oil fraction; a mixing device for combining at least a portion of the heavy vacuum gas oil fraction and at least a portion of the vacuum residuum fraction to form a mixed heavy hydrocarbon fraction; a coker for converting the mixed heavy hydrocarbon fraction to produce anode grade green coke and distillate hydrocarbons; a fractionation system for fractionating the distillate hydrocarbons recovered from the coker into three or more hydrocarbon fractions including a light distillates fraction, a heavy coker gas oil fraction, and a coker recycle fraction.

Other aspects and advantages will be apparent from the following description and the appended claims.

BRIEF DESCRIPTION OF DRAWINGS

Like numerals represent like parts throughout the figures.

DETAILED DESCRIPTION

Figure 1:
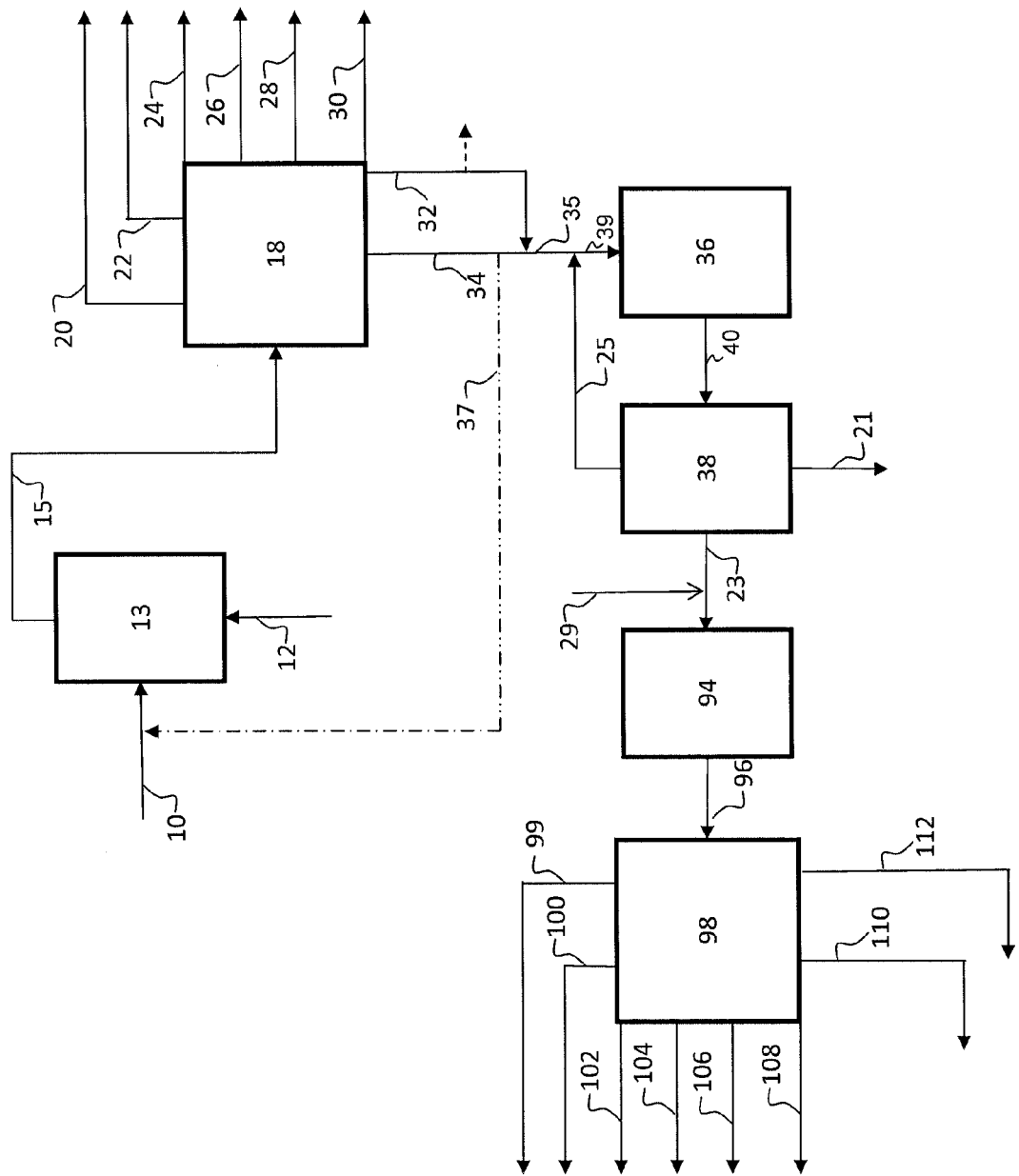
FIG. 1 is a simplified process flow diagram of a process for upgrading residuum hydrocarbon feedstocks according to embodiments disclosed herein.

In one aspect, embodiments herein relate generally to processes for upgrading vacuum residuum streams derived from petroleum, tar sands, shale oils, coal liquids, coal gasification tars and biocrudes, among others. More particularly, embodiments herein relate to processes for producing distillate fuels and anode grade coke from vacuum residua hydrocarbon feedstocks. Even more particularly, embodiments disclosed herein relate to processes for upgrading vacuum residua feedstocks to distillate fuel products using ebullated bed or slurry hydrocracking, delayed coking, and fixed bed catalytic vacuum gas oil upgrading.

Hydroconversion processes disclosed herein may be used for reacting residuum hydrocarbon feedstocks at conditions of elevated temperatures and pressures in the presence of hydrogen and one or more hydroconversion catalyst to convert the feedstock to lower molecular weight products with reduced contaminant (such as sulfur and/or nitrogen) levels. Hydroconversion processes may include, for example, hydrogenation, desulfurization, denitrogenation, cracking, conversion, demetallization, and removal of metals, Conradson Carbon Residue (CCR) or asphaltenes removal, etc.

As used herein, residuum hydrocarbon fractions, or like terms referring to residuum hydrocarbons, are defined as a hydrocarbon fraction having boiling points or a boiling range above about 340° C. but could also include whole heavy crude processing. Residuum hydrocarbon feedstocks that may be used with processes disclosed herein may include various refinery and other hydrocarbon streams such as petroleum atmospheric or vacuum residua, deasphalted oils, deasphalter pitch, hydrocracked atmospheric tower or vacuum tower bottoms, straight run vacuum gas oils, hydrocracked vacuum gas oils, fluid catalytically cracked (FCC) slurry oils, vacuum gas oils from an ebullated bed hydrocracking process, shale-derived oils, coal-derived oils, tar sands bitumen, tall oils, bio-derived crude oils, black oils, as well as other similar hydrocarbon streams, or a combination of these, each of which may be straight run, process derived, hydrocracked, partially desulfurized, and/or partially demetallized streams. In some embodiments, residuum hydrocarbon fractions may include hydrocarbons having a normal boiling point of at least 480° C., at least 524° C., or at least 565° C.

In some embodiments, the residuum feedstock has a metals content of less than about 100 ppmw nickel and less than about 200 ppm vanadium, a sulfur content of less than about 2.5 weight percent, and an asphaltenes content of less than about 12 weight percent. In various embodiments, the residuum may include at least one of petroleum atmospheric or vacuum residua, deasphalted oils, deasphalter pitch, hydrocracked atmospheric tower or vacuum tower bottom, straight run vacuum gas oil, hydrocracked vacuum gas oil, fluid catalytically cracked (FCC) slurry oils, vacuum gas oil from an ebullated bed process, shale-derived oils, coal-derived oils, bioderived crude oils, tar sands bitumen, tall oils, black oils. For example, the residuum hydrocarbon may be derived from one or more of Arab Heavy, Arab Light, Arab Medium, Kuwait Export, Basrah Light, Rubble, Bahrain, Oman, Upper Zakam, REBCO, Kumkol, Ural, Azeri Light, Siberian Light, Siberian Heavy, and Tengiz petroleum crude oils. The shale-derived oils may be generated either in an in situ extraction process or an above ground oil shale retorting process. The coal gasification byproduct oils may be derived from a fixed-bed gasifier or a fluid-bed gasifier or a moving-bed gasifier. The coal-derived oils may be derived from a pyrolysis unit or a hydrothermal liquefaction unit or a thermal hydroliquefaction unit or a catalytic hydroliquefaction unit.

Referring now to FIG. 1, a simplified process flow diagram of a process for upgrading residuum hydrocarbon feedstocks is illustrated. A residuum hydrocarbon fraction 10 (residuum 10) and hydrogen 12 may be fed to a hydroconversion reactor system 13, which may include one or more hydroconversion reactors in series or parallel. In hydroconversion reactor system 13, the residuum and hydrogen may be contacted with a hydroconversion catalyst to convert at least a portion of the residuum to lighter hydrocarbons, demetallize the metals contained in residuum, remove Conradson Carbon Residue, or otherwise convert the residuum to useful products.

Hydroconversion reactors useful in embodiments herein may include ebullated bed hydroconversion reactors or reactor systems, as well as slurry-phase hydrocracking reactor systems, fixed-bed VGO hydrocracking reactor systems, and/or fluidized bed VGO hydrocracking reactor systems. In some embodiments, the fixed bed hydrocracking reactor systems may include one or more as described in U.S. Pat. Nos. 6,797,154; 6,783,660; 6,514,403; 6,224,747; 6,200,462; 6,096,190; 5,925,235; 5,593,570; 5,439,860; and 5,277,793.

Conversion rates in the residuum hydroconversion reactor system 13 may be at least 50% in some embodiments, such as at least 70% or at least 85% in other embodiments. The residuum hydroconversion reactor system 13 may be operated at a pressure about in the range from about 1000 psig to about 4000 psig, an LHSV in the range from about 0.1 L/h/L to about 4.0 L/h/L, a reactor temperature in the range from about 400° C. to about 500° C., a hydrogen/vacuum residuum feedstock ratio of between about 2000-6000 SCF/Bbl, a fresh catalyst makeup rate in the range from about 0.1 to about 0.6 lb/Bbl vacuum resid feedstock. Catalysts useful in hydroconversion reactor system 13 may include one or more of nickel, cobalt, tungsten, molybdenum and combinations thereof, either unsupported or supported on a porous substrate such as silica, alumina, titania, or combinations thereof, as will be described in more detail below.

Following conversion in ebullated bed reactor system 13, the partially converted hydrocarbons may be recovered via flow line 15 and fed to a fractionation system 18 to recover two or more hydrocarbon fractions including at least a vacuum residuum fraction and a heavy vacuum gas oil fraction. As illustrated, fractionation system 18 may be used to recover an offgas 20 containing light hydrocarbon gases and hydrogen sulfide ($H_2S$), a light naphtha fraction 22, a heavy naphtha fraction 24, a kerosene fraction 26, a diesel fraction 28, a light vacuum gas oil fraction 30, a heavy gas oil fraction 32, and a vacuum residuum fraction 34. In some embodiments, a portion of the vacuum residuum fraction 34 may be recycled, such as via flow line 37, for further processing in the ebullated bed hydroconversion reactor system 13. For example, the vacuum residuum fraction 34 or a portion thereof may be combined with at least a portion of the heavy vacuum gas oil fraction 32 to form a mixed heavy hydrocarbon fraction 35. In some embodiments, upstream conditions and feed ratios may be controlled such that the mixed heavy hydrocarbon fraction 35 has a nickel content of less than about 70 ppmw, a vanadium content of less than about 70 ppmw, an asphaltenes/Conradson Carbon Residue (CCR) ratio of less than 0.7 to 1, such as less than 0.5/1 or less than 0.3/1, and a total sulfur content of less than about 24,000 ppmw.

Mixed heavy hydrocarbon fraction 35 may then be fed to a coker system 36, which may be operated at conditions to produce anode grade green coke and distillate hydrocarbons. In some embodiments, coker system 36 may include one or more delayed coking units (delayed cokers).

The coker may be operated at a heater coil outlet temperature of at least 500° C., such as at least 520° C., a pressure in the range from about 20 psig to about 35 psig. The coke drum vapor outlet temperature may be controlled to be at least 450° C., at least 460° C., at least 470° C., or at least 480° C. Drying times after the coking cycle may be at least 2 hours, at least 4 hours, at least 6 hours, or at least 8 hours, in various embodiments. For example, the coke drum vapor outlet temperature may be controlled to be at least 470° C. or 480° C. with drying times of at least 5 hours and preferably at least 8 hours, or at temperatures of at least 450° C. or at least 460° C. with a drying time of at least 6 hours or at least 7 hours, where drying is conducted by passage of a superheated vapor stream through the filled coke drum.

The distillate hydrocarbons may be recovered from coker system 36 via flow line 40 and fractionated in a fractionation system 38 to recover three or more hydrocarbon fractions, such as a light distillates fraction 21, a heavy coker gas oil fraction 23, and a coker recycle fraction 25. In some embodiments, the heavy coker gas oil fraction 23 has a Polycyclic Index based on Ultra Violet Absorption Spectrophotometry of less than 10,000, such as less than about 6000 or less than about 4000.

In some embodiments, the mixed heavy hydrocarbon fraction 35 may be mixed with the coker recycle fraction 25 to form a coker feed mixture 39. As properties of the resulting coke may be affected by the feed quality, it may be desired to limit the amount of coker recycle fraction in the coker feed mixture. In some embodiments, the coker recycle fraction makes up less than 30 weight percent of the coker feed mixture, such as from about 15 weight percent to about 25 weight percent of the coker feed mixture.

The heavy coker gas oil fraction 23 and hydrogen 29 may be contacted with a hydroconversion catalyst in a hydroconversion reactor system 94, which may include one or more fixed bed hydroconversion reactors, to convert at least a portion of the heavy coker gas oil fraction 23 to distillate fuel range hydrocarbons. An effluent 96 may be recovered from the hydroconversion reactor system 94 and fractionated in a fractionation system to form two or more hydrocarbon fractions. For example, effluent 96 may be separated into an offgas 99 containing light hydrocarbon gases, a light naphtha fraction 100, a heavy naphtha fraction 102, a kerosene fraction 104, a diesel fraction 106, a light vacuum gas oil fraction 108, a heavy gas oil fraction 110, and a vacuum residuum fraction 112. One or more of these fractions may optionally be recycled to hydroconversion reactor system 13, fractionation system 38, reactor system 94, or coker system 36.

The anode grade green coke produced according to processes herein may have the following properties: nickel less than about 175 ppm; vanadium less than about 250 ppm; sulfur less than about 35,000 ppmw; Hardgrove Grindability Index (HGI) of less than about 100, and Volatile Combustible Matter of less than about 12 wt %. In order to make anode grade green coke according to embodiments herein, which is much higher in commercial value compared to normal or "fuel grade" petroleum coke, the initial hydroconversion unit and the delayed coking unit have to operate at a specific range of severities dictated by the nature of the particular vacuum residuum feedstock. To produce anode grade coke, the ebullated bed unit must be operated at the proper severity to produce an unconverted vacuum residuum oil suitable for conversion in a Delayed Coking unit to produce a green coke having the correct specifications for producing anode grade coke. The Delayed Coking severity will need to be controlled in order to achieve the specs required for anode grade coke. The combination of correct operating severities in both the ebullated-bed hydrocracking unit and the delayed coking unit is neither obvious nor trivial.

In some embodiments, the coker system 36 may be operated at a Coker Throughput Ratio, defined as the sum of the fresh coker feed rate plus the coker liquid recycle rate divided by the fresh coker feed rate on a liquid volumetric basis, of less than about 1.25/1, such as less than about 1.20/1 or less than about 1.15/1.

Figure 2:
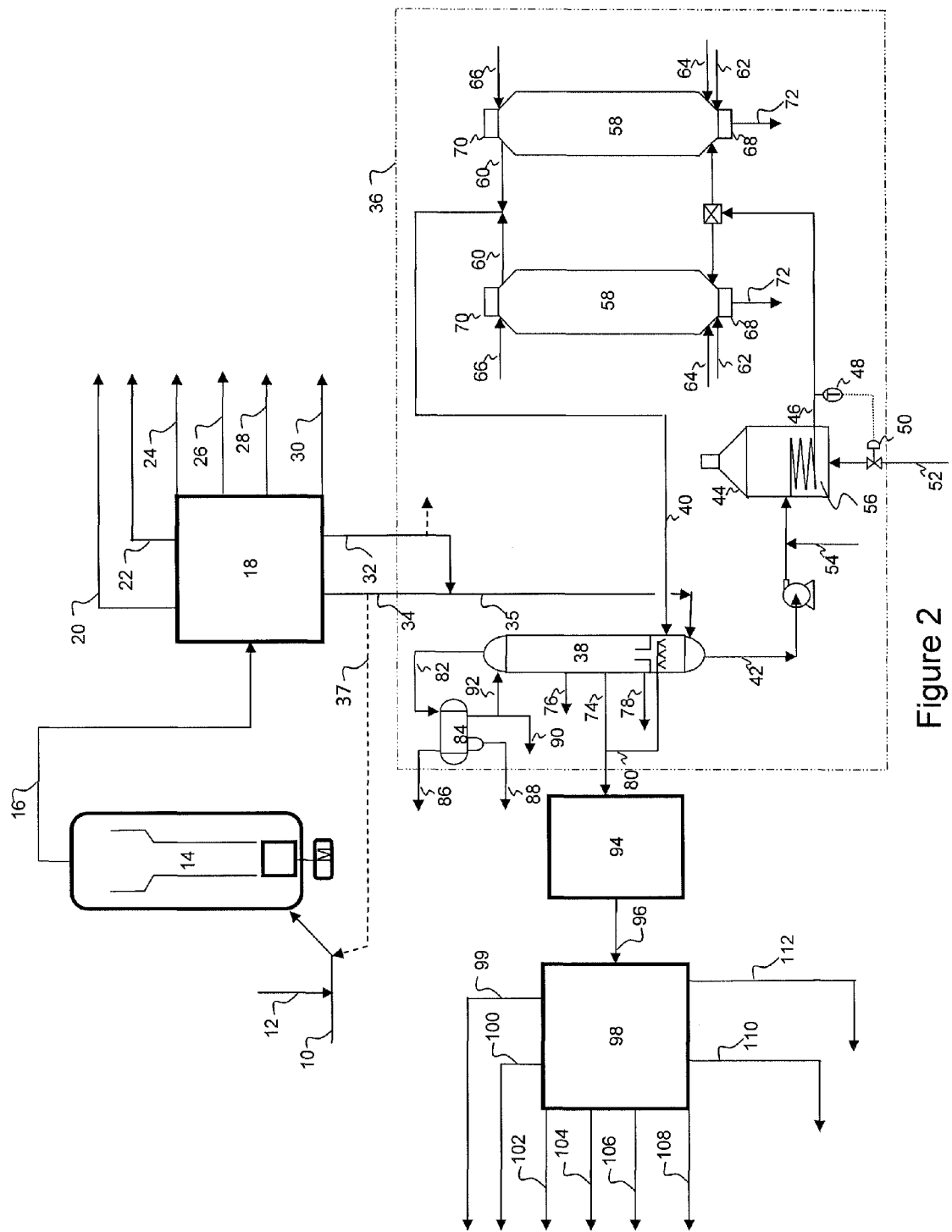
FIG. 2 is a simplified process flow diagram of a process for upgrading residuum hydrocarbon feedstocks according to embodiments disclosed herein.

Referring now to FIG. 2, a simplified process flow diagram of processes according to embodiments herein for upgrading residuum hydrocarbons and producing anode grade green coke is illustrated. A residuum hydrocarbon fraction (residuum) 10 and hydrogen 12 may be fed to an ebullated bed reactor system 14, which may include one or more ebullated bed reactors arranged in series or parallel, where the hydrocarbons and hydrogen are contacted with a hydroconversion catalyst to react at least a portion of the residuum with hydrogen to form lighter hydrocarbons, demetallize the metals contained in residuum, remove Conradson Carbon Residue, or otherwise convert the residuum to useful products.

Reactors in ebullated bed reactor system 14 may be operated at temperatures in the range from about 380° C. to about 450° C., hydrogen partial pressures in the range from about 70 bara to about 170 bara, and liquid hourly space velocities (LHSV) in the range from about 0.2 $h^{-1}$ to about 2.0 $h^{-1}$. Within the ebullated bed reactors, the catalyst may be back mixed and maintained in random motion by the recirculation of the liquid product. This may be accomplished by first separating the recirculated oil from the gaseous products. The oil may then be recirculated by means of an external pump, or, as illustrated, by a pump having an impeller mounted in the bottom head of the reactor.

Target conversions in ebullated bed reactor system 14 may be in the range from about 30 wt % to about 75 wt %, such as greater than about 50%, greater than about 70%, or greater than about 85%, where conversion may depend upon operating conditions and properties of the feedstock being processed. In any event, target conversions should be maintained below the level where sediment formation becomes excessive and thereby prevents continuity of operations. In addition to converting the residuum hydrocarbons to lighter hydrocarbons, sulfur removal may be in the range from about 40 wt % to about 65 wt %, metals removal may be in the range from about 40 wt % to 65 wt % and Conradson Carbon Residue (CCR) removal may be in the range from about 30 wt % to about 60 wt %.

Reactor severity may be defined as the catalyst average temperature in degrees Fahrenheit of the catalysts loaded in the one or more ebullated bed hydrocracking reactors multiplied by the average hydrogen partial pressure of the ebullated bed hydrocracking reactors in Bar absolute and divided by the LHSV in the ebullated bed hydrocracking reactors. The reactor severity of the ebullated bed reactor system 14 may be in the range from about 105,000° F.-Bara-Hr to about 446,000° F.-Bara-Hr.

Following conversion in ebullated bed reactor system 14, the partially converted hydrocarbons may be recovered via flow line 16 as a mixed vapor/liquid effluent and fed to a fractionation system 18 to recover one or more hydrocarbon fractions. As illustrated, fractionation system 18 may be used to recover an offgas 20 containing light hydrocarbon gases and hydrogen sulfide ($H_2S$), a light naphtha fraction 22, a heavy naphtha fraction 24, a kerosene fraction 26, a diesel fraction 28, a light vacuum gas oil fraction 30, a heavy gas oil fraction 32, and a vacuum residuum fraction 34. In some embodiments, a portion of the vacuum residuum fraction 34 may be recycled, such as via flow line 37, for further processing in the ebullated bed hydroconversion reactor system 14.

Fractionation system 18 (not illustrated in detail) may include, for example, a high pressure high temperature (HP/HT) separator to separate the effluent vapor from the effluent liquids. The separated vapor may be routed through gas cooling, purification, and recycle gas compression, or may be first processed through an Integrated Hydroprocessing Reactor System (IHRS), which may include one or more additional hydroconversion reactors, alone or in combination with external distillates and/or distillates generated in the hydrocracking process, and thereafter routed for gas cooling, purification, and compression.

The separated liquid from the HP/HT separator may be flashed and routed to an atmospheric distillation system along with other distillate products recovered from the gas cooling and purification section. The atmospheric tower bottoms, such as hydrocarbons having an initial boiling point of at least about 340° C., such as an initial boiling point in the range from about 340° C. to about 427° C., may then be further processed through a vacuum distillation system to recover vacuum distillates.

The vacuum tower bottoms product, such as hydrocarbons having an initial boiling point of at least about 480° C., such as an initial boiling point in the range from about 480° C. to about 565° C., may then be routed, optionally with a portion of the heavy vacuum gas oil fraction 32, as a mixed coker feedstock 35, to a coking system 36 for production of anode grade green coke.

Coker feedstock 35 may be introduced into the bottom portion of a coker fractionator 38, where it combines with hydrocarbons condensed from coker vapor stream 40. The resulting mixture 42 is then pumped through a coker heater 44, where it is heated to the desired coking temperature, such as between 850° F. and 1100° F., causing partial vaporization and mild cracking of the coker feedstock. The temperature of the heated coker feedstock 46 may be measured and controlled by use of a temperature sensor 48 that sends a signal to a control valve 50 to regulate the amount of fuel 52 fed to the heater 44. If desired, steam or boiler feedwater 54 may be injected into the heater to reduce coke formation in the tubes 56.

The heated coker feedstock 46 may be recovered from the coker heater 44 as a vapor-liquid mixture for feed to coking drums 58. Two or more drums 58 may be used in parallel to provide for continued operation during the operating cycle (coke production, coke recovery (decoking), preparation for next coke production cycle, repeat). Sufficient residence time is provided in the coking drum 58 to allow the thermal cracking and coking reactions to proceed to completion. In this manner, the vapor-liquid mixture is thermally cracked in the coking drum 58 to produce lighter hydrocarbons, which vaporize and exit the coke drum via flow line 60. Petroleum coke and some residuals (e.g. cracked hydrocarbons) remain in the coking drum 58. When the coking drum 58 is sufficiently full of coke, the coking cycle ends. The heated coker feedstock 46 is then switched from the first coking drum 58 to a parallel coking drum to initiate its coking cycle. Meanwhile, the decoking cycle begins in the first coking drum.

In the decoking cycle, the contents of the coking drum are cooled down, remaining volatile hydrocarbons are removed, the coke is drilled or otherwise removed from the coking drum, and the coking drum is prepared for the next coking cycle. Cooling the coke normally occurs in three distinct stages. In the first stage, the coke is cooled and stripped by steam or other stripping media 62 to economically maximize the removal of recoverable hydrocarbons entrained or otherwise remaining in the coke. In the second stage of cooling, water or other cooling media 64 is injected to reduce the coking drum temperature while avoiding thermal shock to the coking drum. Vaporized water from this cooling media further promotes the removal of additional vaporizable hydrocarbons. In the final cooling stage, the coking drum is quenched by water or other quenching media 66 to rapidly lower the coking drum temperatures to conditions favorable for safe coke removal. After the quenching is complete, the bottom and top heads 68, 70 of the coking drum 58 are removed. The anode grade green coke 72 is then removed from the coking drum. After coke removal, the coking drum heads 68, 70 are replaced, the coking drum 58 is preheated, and otherwise readied for the next coking cycle.

The lighter hydrocarbon vapors recovered as an overheads fraction 60 from coking drum 58 are then transferred to the coker fractionator 38 as coker vapor stream 40, where they are separated into two or more hydrocarbon fractions and recovered. For example, a heavy coker gas oil (HCGO) fraction 74 and a light coker gas oil (LCGO) fraction 76 may be drawn off the fractionator at the desired boiling temperature ranges. HCGO may include, for example, hydrocarbons boiling in the range from 650-870° F. LCGO may include, for example, hydrocarbons boiling in the range from 400-650° F. In some embodiments, other hydrocarbon fractions may also be recovered from coker fractionator 38, such as a quench oil fraction 78, which may include hydrocarbons heavier than HCGO, and/or a wash oil fraction 80. The fractionator overhead stream, coker wet gas fraction 82, goes to a separator 84, where it is separated into a dry gas fraction 86, a water/aqueous fraction 88, and a naphtha fraction 90. A portion of naphtha fraction 90 may be returned to the fractionator as a reflux 92. Other fractionation schemes may also be used, and may result in light petroleum gas fractions, coker naphtha fractions, coker diesel fractions, and/or other hydrocarbon fractions as may be desired.

The temperature of the materials within the coking drum 58 throughout the coke formation stage and the drying stage may be used to control the type of coke crystalline structure and the amount of volatile combustible material in the coke. The temperature of the vapors leaving the coke drum via flow line 60 is thus an important control parameter used to represent the temperature of the materials within the coking drum 58 during the coking process, and may be controlled as described herein.

The temperature of the coking drum overhead vapor fraction 60 may be used to monitor and control the coking process and the coke product quality (VCM content, crystalline structure, etc.). In some embodiments, the temperature of the vapor product recovered from the coking drum may be controlled, for example, by using a digital control system (DCS) or other process control systems to be within the range from about 700° F. to about 900° F.; in the range from about 725° F. to about 875° F. in other embodiments; in the range from about 750° F. to about 850° F. in other embodiments; and in the range from about 775° F. to about 800° F. in yet other embodiments. In some embodiments, the coker heater outlet temperature may be in the range from about 900° F. to about 1100° F. The DCS may also be used to control the decoking cycle, as described below.

Various chemical and/or biological agents may be added to the coking process to inhibit the formation of shot coke and/or promote the formation of desirable sponge coke. In particular embodiments, an anti-foaming agent may be added, such as a silicon-based additive. The chemical and/or biological agents may be added at any point in the process.

Following conversion and fractionation in coker system 36 and fractionation system 38, the heavy coker gas oil fraction 74 may be fed to a hydroconversion reactor system 94, which may include one or more fixed bed hydroconversion reactors. The fixed bed hydroconversion reactors 94 may contain hydroprocessing catalysts tailored to one or more hydroconversion reactions such as hydrocracking, hydrodesulfurization, hydrodenitrogenation, olefins saturation, hydrodeoxygenation and hydrodearomatization. In some embodiments, the fixed bed hydroconversion reactors 94 may contain a mixture of hydrotreating catalysts and hydrocracking catalysts. Examples of catalysts which may be utilized, but are not limited to, may be found in U.S. Pat. Nos. 4,990,243; 5,215,955;and 5,177,047, all of which are hereby incorporated by reference in their entirety. In some embodiments, the fixed bed hydroconversion reactors 94 may not provide any demetallization and demetallization catalysts may not be necessary.

Following reaction, effluent 96 recovered from hydroconversion reactor system 94 may be sent to a fractionation system 98 for separation of the effluent into two or more hydrocarbon fractions. For example, effluent 96 may be separated into an offgas 99 containing light hydrocarbon gases, a light naphtha fraction 100, a heavy naphtha fraction 102, a kerosene fraction 104, a diesel fraction 106, a light vacuum gas oil fraction 108, a heavy gas oil fraction 110, and a vacuum residuum fraction 112. One or more of these fractions may optionally be recycled to hydroconversion reactor system 14, fractionation system 38, reactor system 94, or coker system 36.

Figure 3:
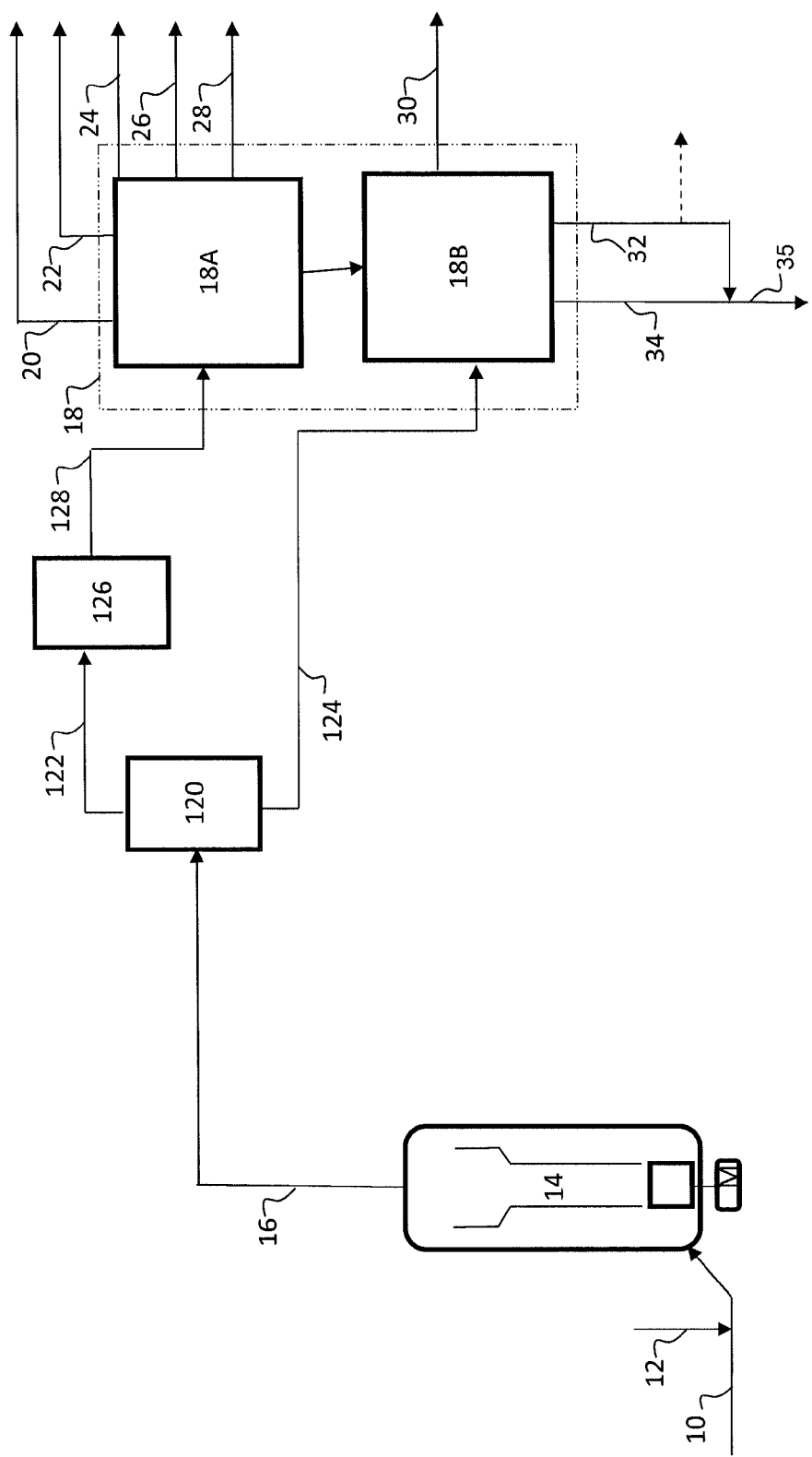
FIG. 3 is a simplified process flow diagram of a portion of a process for upgrading residuum hydrocarbon feedstocks according to embodiments herein.

FIG. 3 illustrate one embodiment for the IHRS mentioned above; however, other embodiments may be readily envisioned by those skilled in the art based on the following description. The partially converted hydrocarbons recovered via flow line 16 from ebullated bed reactor system 14 may be cooled in a heat exchanger (not shown) and fed to a HP/HT V/L separator 120 where a vapor stream 122 including the light products and distillates boiling below about 1000° F. normal boiling point and a liquid stream 124 including unconverted residuum may be separated and processed separately in downstream equipment. Vapor stream 122 may be fed to a fixed bed hydroprocessing reactor 126 to carry out hydrotreating, hydrocracking or a combination thereof. An effluent stream 128 from the IHRS fixed bed reactor system 126 is fed to the atmospheric tower 18A of fractionation system 18 to recover various fractions as described with respect to FIG. 2. The liquid stream 124 may be cooled in a heat exchanger (not shown) and depressurized in a pressure letdown system (not shown) before being fed to a vacuum fractionation system 18B of fractionation system 18 to recover various fractions as described with respect to FIG. 2.

Hydroconversion catalyst compositions for use in the hydroconversion process according to embodiments disclosed herein are well known to those skilled in the art and several are commercially available from W.R. Grace & Co., Criterion Catalysts & Technologies, and Albemarle, among others. Suitable hydroconversion catalysts may include one or more elements selected from Groups 4-12 of the Periodic Table of the Elements. In some embodiments, hydroconversion catalysts according to embodiments disclosed herein may comprise, consist of, or consist essentially of one or more of nickel, cobalt, tungsten, molybdenum and combinations thereof, either unsupported or supported on a porous substrate such as silica, alumina, titania, or combinations thereof. As supplied from a manufacturer or as resulting from a regeneration process, the hydroconversion catalysts may be in the form of metal oxides, for example. In some embodiments, the hydroconversion catalysts may be pre-sulfided and/or pre-conditioned prior to introduction to the hydrocracking reactor(s).

Distillate hydrotreating catalysts that may be useful include catalyst selected from those elements known to provide catalytic hydrogenation activity. At least one metal component selected from Group 8-10 elements and/or from Group 6 elements is generally chosen. Group 6 elements may include chromium, molybdenum and tungsten. Group 8-10 elements may include iron, cobalt, nickel, ruthenium, rhodium, palladium, osmium, iridium and platinum. The amount(s) of hydrogenation component(s) in the catalyst suitably range from about 0.5% to about 10% by weight of Group 8-10 metal component(s) and from about 5% to about 25% by weight of Group 6 metal component(s), calculated as metal oxide(s) per 100 parts by weight of total catalyst, where the percentages by weight are based on the weight of the catalyst before sulfiding. The hydrogenation components in the catalyst may be in the oxidic and/or the sulphidic form. If a combination of at least a Group 6 and a Group 8 metal component is present as (mixed) oxides, it will be subjected to a sulfiding treatment prior to proper use in hydrocracking. In some embodiments, the catalyst comprises one or more components of nickel and/or cobalt and one or more components of molybdenum and/or tungsten or one or more components of platinum and/or palladium. Catalysts containing nickel and molybdenum, nickel and tungsten, platinum and/or palladium are useful.

Residue hydrotreating catalyst that may be useful include catalysts generally composed of a hydrogenation component, selected from Group 6 elements (such as molybdenum and/or tungsten) and Group 8-10 elements (such as cobalt and/or nickel), or a mixture thereof, which may be supported on an alumina support. Phosphorous (Group 15) oxide is optionally present as an active ingredient. A typical catalyst may contain from 3 to 35 wt % hydrogenation components, with an alumina binder. The catalyst pellets may range in size from 1/32 inch to 1/8 inch, and may be of a spherical, extruded, trilobate or quadrilobate shape. In some embodiments, the feed passing through the catalyst zone contacts first a catalyst preselected for metals removal, though some sulfur, nitrogen and aromatics removal may also occur. Subsequent catalyst layers may be used for sulfur and nitrogen removal, though they would also be expected to catalyze the removal of metals and/or cracking reactions. Catalyst layer(s) for demetallization, when present, may comprise catalyst(s) having an average pore size ranging from 125 to 225 Angstroms and a pore volume ranging from 0.5-1.1 cm$^3$/g. Catalyst layer(s) for denitrogenation/desulfurization may comprise catalyst(s) having an average pore size ranging from 100 to 190 Angstroms with a pore volume of 0.5-1.1 cm$^3$/g. U.S. Pat. No. 4,990,243 describes a hydrotreating catalyst having a pore size of at least about 60 Angstroms, and preferably from about 75 Angstroms to about 120 Angstroms. A demetallization catalyst useful for the present process is described, for example, in U.S. Pat. No. 4,976,848, the entire disclosure of which is incorporated herein by reference for all purposes. Likewise, catalysts useful for desulfurization of heavy streams are described, for example, in U.S. Pat. Nos. 5,215,955 and 5,177,047, the entire disclosures of which are incorporated herein by reference for all purposes. Catalysts useful for desulfurization of middle distillate, vacuum gas oil streams and naphtha streams are described, for example, in U.S. Pat. No. 4,990,243, the entire disclosures of which are incorporated herein by reference for all purposes.

Useful residue hydrotreating catalysts include catalysts having a porous refractory base made up of alumina, silica, phosphorous, or various combinations of these. One or more types of catalysts may be used as residue hydrotreating catalyst, and where two or more catalysts are used, the catalysts may be present in the reactor zone as layers. The catalysts in the lower layer(s) may have good demetallization activity. The catalysts may also have hydrogenation and desulfurization activity, and it may be advantageous to use large pore size catalysts to maximize the removal of metals. Catalysts having these characteristics are not optimal for the removal of Conradson Carbon Residue and sulfur. The average pore size for catalyst in the lower layer or layers will usually be at least 60 Angstroms and in many cases will be considerably larger. The catalyst may contain a metal or combination of metals such as nickel, molybdenum, or cobalt. Catalysts useful in the lower layer or layers are described in U.S. Pat. Nos. 5,071,805 5,215,955, and 5,472,928. For example, those catalysts as described in U.S. Pat. No. 5,472,928 and having at least 20% of the pores in the range of 130 to 170 Angstroms, based on the nitrogen method, may be useful in the lower catalysts layer(s). The catalysts present in the upper layer or layers of the catalyst zone should have greater hydrogenation activity as compared to catalysts in the lower layer or layers. Consequently catalysts useful in the upper layer or layers may be characterized by smaller pore sizes and greater Conradson Carbon Residue removal, denitrogenation and desulfurization activity. Typically, the catalysts will contain metals such as, for example, nickel, tungsten, and molybdenum to enhance the hydrogenation activity. For example, those catalysts as described in U.S. Pat. No. 5,472,928 and having at least 30% of the pores in the range of 95 to 135 Angstroms, based on the nitrogen method, may be useful in the upper catalysts layers. The catalysts may be shaped catalysts or spherical catalysts. In addition, dense, less friable catalysts may be used in the upflow fixed catalyst zones to minimize breakage of the catalyst particles and the entrainment of particulates in the product recovered from the reactor.

One skilled in the art will recognize that the various catalyst layers may not be made up of only a single catalyst, but may be composed of an intermixture of different catalysts to achieve the optimal level of metals or Conradson Carbon Residue removal and desulfurization for that layer. Although some hydrogenation will occur in the lower portion of the zone, the removal of Conradson Carbon Residue, nitrogen, and sulfur may take place primarily in the upper layer or layers. Obviously additional metals removal also will take place. The specific catalyst or catalyst mixture selected for each layer, the number of layers in the zone, the proportional volume in the bed of each layer, and the specific hydrotreating conditions selected will depend on the feedstock being processed by the unit, the desired product to be recovered, as well as commercial considerations such as cost of the catalyst. All of these parameters are within the skill of a person engaged in the petroleum refining industry and should not need further elaboration here.

While described above with respect to separate fractionation systems 18, 38, 98, embodiments disclosed herein also contemplate fractionating two or more of effluents 16, 35, 40, 96 in a common fractionation system. For example, effluents 16, 96 may be fed into a common gas cooling, purification, and compression loop before further processing in an atmospheric tower and a vacuum tower as described above.

As described above, embodiments herein relate to a system for upgrading residuum hydrocarbon feedstocks. The system may include: a residuum hydroconversion reactor system for contacting a residuum hydrocarbon and hydrogen with a hydroconversion catalyst; a fractionation system for separating an effluent recovered from the residuum hydroconversion reactor system into two or more hydrocarbon fractions including at least a vacuum residuum fraction and a heavy vacuum gas oil fraction; a mixing device for combining at least a portion of the heavy vacuum gas oil fraction and at least a portion of the vacuum residuum fraction to form a mixed heavy hydrocarbon fraction; a coker for converting the mixed heavy hydrocarbon fraction to produce anode grade green coke and distillate hydrocarbons; and a fractionation system for fractionating the distillate hydrocarbons recovered from the coker into three or more hydrocarbon fractions including a light distillates fraction, a heavy coker gas oil fraction, and a coker recycle fraction.

Systems disclosed herein may also include a mixing device for admixing the mixed heavy hydrocarbon fraction with the coker recycle fraction to form a coker feed mixture. Mixing devices useful herein may include tees, mixing tees, pumps, agitated vessels, or other devices as known in the art to combine and intimately mix two (possibly viscous) liquid streams.

Systems disclosed herein may also include a flow measurement and control system for controlling the coker recycle fraction to be less than 30 weight percent of the coker feed mixture, such as to be in the range from about 15 weight percent to about 25 weight percent of the coker feed mixture.

The system may also include: a hydroconversion reactor for contacting the heavy coker gas oil fraction and hydrogen with a hydroconversion catalyst to convert at least a portion of the heavy coker gas oil fraction to distillate fuel range hydrocarbons; and a separation system for fractionating an effluent from the hydroconversion reactor to form two or more hydrocarbon fractions.

Systems herein may also include an operating system configured to control the residuum hydroconversion reactor system to produce the mixed heavy hydrocarbon fraction having a nickel content of less than about 70 ppmw, a vanadium content of less than about 70 ppmw, an asphaltenes/Conradson Carbon Residue (CCR) ratio of less than 0.7 to 1 and preferably less than 0.5/1 and more preferably less than 0.3/1, and a total sulfur content of less than about 24,000 ppmw. The operating system may also be configured for one or more of: controlling the conversion rate in the residuum hydroconversion reactor system to be at least 50% and more preferably at least 70% and more preferably at least 85%; operating the hydroconversion reactor system at a pressure about in the range from about 1000 psig to about 4000 psig, an LHSV in the range from about 0.1 L/h/L to about 4.0 L/h/L, a reactor temperature in the range from about 400° C. to about 500° C., a hydrogen/vacuum residuum feedstock ratio of between about 2000-6000 SCF/Bbl, a fresh catalyst makeup rate in the range from about 0.1 to about 0.6 lb/Bbl vacuum resid feedstock; operating the coker at a heater coil outlet temperature of at least 500° C. or at least 520° C.; a pressure of about between 20-35 psig and with a drying time after the coking cycle of at least 2 hours or at least 4 hours or at least 6 hours or at least 8 hours; operating the coke drum vapor outlet temperature in said coking unit to be at least 470° C. or at least 480° C. for a drying time of at least 5 hours and preferably at least 8 hours or at least 450° C. or at least 460° C. for a drying time of at least 6 hours or at least 7 hours by passage of a superheated vapor stream through the filled coke drum; controlling the Coker Throughput Ratio, defined as the sum of the fresh coker feed rate plus the coker liquid recycle rate divided by the fresh coker feed rate on a liquid volumetric basis, to be less than about 1.25/1 and preferably less than 1.20/1 and more preferably less than about 1.15/1.

As described above, embodiments herein relate to the conversion of heavy hydrocarbon feedstocks to produce distillate range hydrocarbons and anode grade green coke. As an example of the above described systems and processes, atmospheric and/or vacuum residue derived from the fractionation of crude oil is heated, mixed with hydrogen rich treat gas and charged to the hydrocracking stage which consists of a single or may utilize a multiplicity of reactors arranged in parallel and/or series. Here the residue fraction, typically defined as having a boiling point above 524° C. (975° F.) and preferably above 566° C. (1050° F.) is hydrocracked under hydrogen partial pressures of 70 to 170 bara (1000-2400 psia), temperatures of 380 to 450° C. at a LHSV of 0.2 to 2.0 h$^{-1}$ in the presence of catalyst.

Within the ebullated bed, the catalyst is back mixed and maintained in random motion by the recirculation of liquid product. This is accomplished by first separating the recirculated oil from the gaseous products. The oil is then recirculated by means of an external pump or a pump whose impeller is mounted in the bottom head of the reactor.

The target residue conversion from the hydrocracking stage may be in the range of 50 to 88 wt % depending on the feedstock being processed. It is anticipated that metals removal will be in the range of 80 to 90%, sulfur removal will be in the range from 80 to 90% and Conradson Carbon Residue (CCR) removal in the range of 45 to 65%.

The liquid and vapor effluent from the hydrocracking reactors enters the high pressure high temperature separator (i.e. HP/HT Separator). The separated vapor is either, directly routed through a common gas cooling, purification and recycle gas compression system, or first processed through an Integrated Hydroprocessing Reactor System, alone or in combination with either external distillates and/or distillates generated in the hydrocracking process and, thereafter, routed a common gas cooling, purification and compression system.

The separated liquid from the HP/HT Separator is then flashed and routed to the Atmospheric Distillation System along with other distillate products recovered from the gas cooling and purification section. The atmospheric tower bottoms (i.e., nominally 360° C. to 427° C.+ boiling fraction) is further processed through a Vacuum Distillation System to recover vacuum distillates. In this case, the vacuum tower bottoms product (i.e. nominally 482° C. to 565° C.+ boiling fraction) is then routed to a Delayed Coking Unit either hot, or after cooling, such as through direct heat exchange or by the direct injection of a portion of the residue feed into the vacuum tower bottoms product. The latter route thereby eliminates the need for direct heat exchange of the vacuum tower bottoms product, which is known to be fouling.

In the Delayed Coking Unit, the unconverted oil and the heavy vacuum gas oil normally flows through the preheat exchangers to the bottom of the main fractionator under level control. There the feed mixes with the internal recycle liquid (quantity controlled within the range of 15% to 25% of fresh feed) condensed from the coke drum effluent. This combined feed and recycle is pumped from the bottom of the fractionator through the coking heater where each pass is flow controlled. A controlled quantity of high pressure steam is injected into each heater pass to assure satisfactory velocity in order to minimize coking in the heater tubes. The prime function of the coking heater is to quickly heat the feed to the required coking temperature to initiate the cracking reaction without premature coke formation in the heater tubes.

The effluent from the coking heater flows through a switch valve into the bottom of one of the two coke drums where further cracking and then polymerization takes place to form coke. Each drum is designed to be filled to a safe operating level with coke produced during the coking cycle. Antifoam is injected into the coke drum during the latter part of the filling cycle to minimize the carryover of foam, coke fines, and pitch into the fractionator. The coke drum is operated in cycles to maintain continuity of operation, with a minimum cycle time of 24 hours being employed in this application. The operation of each coke drum is staggered. One of the drums of each pair is always in service to receive the coking heater effluent.

The vapor from the coke drum is quenched by heavy gas oil to stop the cracking and polymerization reactions, and thereby minimize coke formation in the overhead line from the coke drums to the fractionator. The fractionator is divided into two sections by the heavy gas oil draw-off pan. The upper section consists of valve trays; the lower section contains special internals consisting of a two-tiered fractionator spray chamber. The coke drum vapor enters the fractionator below the spray headers. The vapor flows upward through a specially designed tower bottom section where it contacts the down flowing droplets of reflux liquid and de-superheats the vapor. The internal recycle stream thus condensed is collected at the bottom of the tower where it mixes with the fresh feed charge. Vapor leaving the lower section of the tower flows to the upper section through the risers in the heavy gas oil draw-off pan. This vapor consists of light hydrocarbons, naphtha, kerosene, light and heavy gas oils, vaporized reflux, and steam. This mixture is fractionated in the upper section of the tower.

The drying portion of the cycle provides uniform heat distribution and produces a more uniform coke structure and density and allows the unreacted tar at the reaction front inside the coke drum to complete the coking reaction. The drying of the coke bed increases the mechanical strength of coke thus increasing coke hardness (improving HGI) and reducing volatile combustible matter (VCM) of green coke before steam out to the main column or to the blowdown system.

After an empty coke drum is filled to the proper level, the effluent from the coking heater is switched to another preheated empty coke drum by means of switch valve(s). The contents of the full drum are then "dried", for approximately 5 to 8 hours using superheated vapor such as coker gas oil vapors, coker naphtha, steam, and any other suitable superheated non-coking hydrocarbon vapors. After drying, the coke drum filled with green anode coke is steamed initially to the main column and then to the blowdown system followed by cooling/quenching operation. Then the coke drum is hydraulically decoked.

The superheated drying medium may consist of superheated steam, or superheated vapors generated from the non-coking portion of the coker C5+ liquid or any other hydrocarbon stream that can be vaporized and superheated without the risk of coking. The drying medium shall be introduced into the coke drum through the feed inlet line, but via a separate line than the residual oil feed line. The superheated vapor temperature is controlled around at approximately 5IOC at the inlet to the coke drum. The drying cycle continues until a coke drum overhead temperature between 470 to 480 C is reached and maintained after 4 to 8 hours of drying time and more preferably 450 to 460 C for 4-5 hours. Compared to the increased throughput ratio mode, e.g., high coker liquids recycle rates, the use of a non-coking medium allows heat distribution without increasing coke production and loss of liquid yield.

As described above, embodiments herein provide systems and processes for the conversion of heavy hydrocarbon feedstocks to produce distillate range hydrocarbons and anode grade green coke. More specifically, processes disclosed herein provide an processes for upgrading vacuum residua feedstocks to distillate fuel products using ebullated-bed or slurry hydrocracking, delayed coking, and fixed-bed catalytic VGO upgrading technologies to maximize coker distillate yields, co-produce high quality anode grade coke without resorting to use of very high coker liquids recycle rates, and co-produce high quality heavy coker gas oil feeds for downstream catalytic VGO upgrading, such as via fixed-bed hydrocracking or fluid-bed catalytic cracking, to distillate fuels.

Processes disclosed herein have several advantages. For example, processes disclosed herein may include one or more of the following advantages as compared to present state-of-the-art flowschemes, including: higher overall distillate yields in the coking units and hydrocracking units; simultaneous co-production of high grade anode coke; achievement of anode coke quality without the need for high coker liquids recycle rates; and production of high quality coker gas oils. a distillate yields advantage, resulting from higher conversions in the hydroconversion reactor system for converting residuum feedstocks and operation of the coker to make anode grade coke under conditions that maximize distillate yields by using relatively low coker liquids recycle rates. Embodiments herein may advantageously not use light solvents to dilute the asphaltenes in the feed to the Coking Unit. Further, processes herein may produce an unexpectedly low polynuclear aromatics content in the HCGO fraction, which allows its effective and economically advantageous upgrading in a fixed-bed hydrocracker rather than in a fluid catalytic cracker.

Further, the ebullated bed upstream of the Delayed Coking unit may effectively debottleneck the Delayed Coking unit by reducing the amount of required vacuum residua to be processed while at the same time producing a much higher value coke product. Without this combination, there would be incremental production of low value coke that would adversely impact the refinery economics.

EXAMPLE

According to one or more embodiments of the present disclosure is the use of the hydroprocessed vacuum resid fraction from hydrocracking of virgin vacuum resid feedstocks, such as in an ebullated-bed hydrocracker, which has unique properties that virgin and thermally cracked residua do not have with regards to their ability to simultaneously produce anode grade coke and high distillate yields in a delayed coking unit. Said delayed coking unit would be operated at economically desirable reaction conditions to produce anode grade coke. The following experimental example illustrates the comparative performance of feeding a virgin vacuum resid and the feedstock of this invention to a delayed coking unit.

I. Feedstock Compositions

A refiner processes a mixture of petroleum crude oils as shown in Table I-1 below. The crude is fractionated in an atmospheric tower to produce virgin distillates and an atmospheric virgin resid fraction. The atmospheric virgin resid is fractionated in a vacuum tower to produce vacuum gas oil distillates and a virgin vacuum resid.

TABLE I-1

| Crude Type | Lvol % |
|---|---|
| Basrah Light | 53 |
| Kuwait | 14 |
| Arabian Heavy | 11 |
| Upper Zakam | 10 |
| Banoco Arabian Medium | 7 |
| Oman | 5 |
| Total | 100 |

The properties of the virgin vacuum resid are shown in the first column of Table I-2 below.

TABLE I-2

| Description | Virgin Vacuum Resid Feed to Coker | Mixed Heavy Feed to Coker |
|---|---|---|
| Conradson Carbon Residue | 24.0 | 19.7 |
| API Gravity | 4.1 | 7.3 |
| Sulfur, wt % | 5.1 | 2.28 |
| Asphaltenes, wt % | 12.1 | 7.7 |
| Nickel, wppm | 41.0 | 17.0 |
| Vanadium, wppm | 130.0 | 18.1 |

II. Feedstocks

The virgin vacuum resid fraction is subjected to ebullated-bed hydrocracking at 2200 psig, 1.2 LHSV, 440° C. reactor temperature and 6000 scf/bbl H2 treat rate over a nickel-based hydroconversion catalyst. The recovered liquid products are subjected to atmospheric fractionation and vacuum fractionation wherein a hydroprocessed vacuum resid (HVR) and a hydroprocessed vacuum gas oil (HVGO) are recovered. The 900-1050° F. hydroprocessed VGO is blended with the 1050° F.+ hydroprocessed vacuum resid in a ratio of 0.8/1 by weight. The said blend is the mixture of heavy hydrocarbon feed (stream 35, FIG. 1) fed to the Coker. The properties of said stream are shown in the second column of Table I-2.

III. Coking of Virgin Vacuum Resid

The virgin vacuum resid fraction is subjected to delayed coking at 860° F. average coke bed temperature, 35 psig coke drum pressure and a recycle rate, defined as the weight ratio of the sum of the fresh coker feed and the coker liquids recycle rates to that of the fresh coker feed rate, of 1.25. The coke product failed to meet the anode grade coke specifications as shown in Table III-1 below.

TABLE III-1

| Property | Coke from Virgin Vacuum Resid | Anode Coke Specs |
|---|---|---|
| Sulfur, wt % | 6.7 | <3.5 |
| Nickel, wppm | 136 | <175 |
| Vanadium, wppm | 433 | <250 |
| Hardgrove Grindability Index | 108 | <100 |

IV. Coking of Hydroprocessed VGO/VR Mix: Effect of Coke Drum Pressure

A series of experiments were made to show the effects of coke drum pressure on coke quality and C5+ liquids yields at 1.25 coker liquids recycle rate and 862-869° F. average coke bed temperature. In both tests, anode coke grade specs were met. By decreasing coke drum pressure from 35 to 20 psig, total C5+ liquid yields increase by about 5-6 percentage points with a concomitant decrease in coke yields as shown in Table IV-1.

TABLE IV-1

| Run Number | 134 | 135 |
|---|---|---|
| Coke Drum Pressure | 20 | 35 |
| Recycle Rate (FF-Rec)/FF) | 1.25 | 1.25 |
| Average Coke Bed Temperature, ° F. | 862 | 869 |
| Total C4− Gas, wt % | 9.55 | 10.39 |
| Total C5+ Liquid, wt % | 59.69 | 54.11 |
| Total Coke, wt % | 30.76 | 35.51 |
| Key Coke Properties Related to Anode Grade Coke Quality | | |
| Sulfur, wt % | 3.1 | 3.2 |
| Nickel, wppm | 66 | 68 |
| Vanadium, wppm | 75 | 68 |
| Hardgrove Grindability Index | 61 | 58 |

V. Coking of Hydroprocessed VGO/VR Mix: Effect of Liquid Recycle Rate

A series of experiments were made to show the effects of coker liquid recycle rate on coke quality and C5+ liquids yields at 20 psig coke drum pressure and 862-869° F. average coke bed temperature. In both tests, anode coke grade specs were met. By decreasing coker liquids recycle rate from 1.35 to 1.25, total C5+ liquid yields increase by about 4 percentage points with a concomitant decrease in coke yields as shown in Table V-1 below.

TABLE V-1

| Run Number | 134 | 136 |
|---|---|---|
| Coke Drum Pressure | 20 | 20 |
| Recycle Rate (FF = Rec)/FF) | 1.25 | 1.35 |
| Average Coke Bed Temperature, ° F. | 862 | 869 |
| Total C4− Gas, wt % | 9.55 | 9.17 |
| Total C5+ Liquid, wt % | 59.69 | 55.53 |
| Total Coke, wt % | 30.76 | 35.29 |
| Key Coke Properties Related to Anode Grade Coke Quality | | |
| Sulfur, wt % | 3.1 | 3.3 |
| Nickel, wppm | 66 | 64 |
| Vanadium, wppm | 75 | 63 |
| Hardgrove Grindability Index | 61 | 58 |

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed:

1. A process for upgrading residuum hydrocarbon feedstocks, comprising:
   contacting a residuum hydrocarbon and hydrogen with a hydroconversion catalyst in an residuum hydroconversion reactor system;
   recovering an effluent from the residuum hydroconversion reactor system;
   separating the effluent from the residuum hydroconversion reactor system to recover two or more hydrocarbon fractions including at least a vacuum residuum fraction and a heavy vacuum gas oil fraction;
   combining at least a portion of the heavy vacuum gas oil fraction and at least a portion of the vacuum residuum fraction to form a mixed heavy hydrocarbon fraction;
   feeding at least a portion of the mixed heavy hydrocarbon fraction to a coker;
   operating the coker at conditions to produce anode grade green coke and distillate hydrocarbons;
   recovering the distillate hydrocarbons from the coker;
   fractionating the distillate hydrocarbons recovered from the coker to recover three or more hydrocarbon fractions including a light distillates fraction, a heavy coker gas oil fraction, and a coker recycle fraction,
   wherein the said vacuum residuum feedstock is derived from one or more of Arab Heavy, Arab Light, Banoco Arab Medium, Kuwait Export, Basrah Light, Rubble, Bahrain, Oman, Upper Zakam, REBCO, Kumkol, Azeri Light, Siberian Light, Siberian Heavy, and Tengiz petroleum crude oils.

2. The process of claim 1, further comprising admixing the mixed heavy hydrocarbon fraction with the coker recycle fraction to form a coker feed mixture.

3. The process of claim 2, wherein the coker recycle fraction is less than 30 weight percent of the coker feed mixture.

4. The process of claim 2, wherein the coker recycle fraction is from about 15 weight percent to about 25 weight percent of the coker feed mixture.

5. The process of claim 1, further comprising:
   contacting the heavy coker gas oil fraction and hydrogen with a hydroconversion catalyst in a hydroconversion reactor to convert at least a portion of the heavy coker gas oil fraction to distillate fuel range hydrocarbons;
   recovering an effluent from the hydroconversion reactor; and
   fractionating the effluent to form two or more hydrocarbon fractions.

6. The process of claim 1, wherein the heavy coker gas oil fraction has a Polycyclic Index based on Ultra Violet Absorption Spectrophotometry of less than 10,000.

7. The process of claim 1, wherein the residuum hydrocarbon has a metals content of less than about 100 ppmw nickel and less than about 200 ppm vanadium, a sulfur content of less than about 2.5 weight percent, and an asphaltenes content of less than about 12 weight percent.

8. The process of claim 1, wherein the mixed heavy hydrocarbon fraction has a nickel content of less than about 70 ppmw, a vanadium content of less than about 70 ppmw, an asphaltenes/Conradson Carbon Residue (CCR) ratio of less than 0.7 to 1, and a total sulfur content of less than about 24,000 ppmw.

9. The process of claim 1, wherein the residuum hydrocarbon comprises at least one of petroleum atmospheric or vacuum residua, deasphalted oils, deasphalter pitch, hydrocracked atmospheric tower or vacuum tower bottom, straight run vacuum gas oil, hydrocracked vacuum gas oil, fluid catalytically cracked (FCC) slurry oils, vacuum gas oil from an ebullated bed process, shale-derived oils, coal-derived oils, bioderived crude oils, tar sands bitumen, tall oils, black oils.

10. The process of claim 1, wherein the coker is a delayed coker.

11. The process of claim 1, wherein the residuum hydroconversion reactor system comprises an ebullated bed hydroconversion reactor system.

12. The process of claim 1, wherein the residuum hydroconversion reactor system comprises a slurry-phase hydrocracking process.

13. The process of claim 1, wherein the hydroconversion reactor comprises at least one of a fixed-bed vacuum gas oil (VGO) hydrocracking reactor system, a fluidized bed VGO hydrocracking reactor system.

14. The processes of claim 1, wherein the conversion rate in the residuum hydroconversion reactor system is at least 50%.

15. The processes of claim 1, wherein the residuum hydroconversion reactor system is operated at:
a pressure in the range from about 1000 psig to about 4000 psig;
LHSV in the range from about 0.1 to about 4.0 L/h/L;
a reactor temperature in the range from about 400° C. to about 500° C.;
a hydrogen/vacuum residuum feedstock ratio of about between 2000-6000 SCF/Bbl;
a fresh catalyst makeup rate in the range from about 0.1 to 0.6 lb/Bbl vacuum resid feedstock; and
using a catalyst comprised of one or more of nickel, cobalt, tungsten, molybdenum and combinations thereof, either unsupported or supported on a porous substrate such as silica, alumina, titania, or combinations thereof.

16. The processes of claim 1, wherein the coker is operated at:
a heater coil outlet temperature of at least 500° C.;
a pressure in the range from about 20 psig to about 35 psig; and
with a drying time after the coking cycle of at least 2 hours.

17. The processes of claim 1, wherein the coke drum vapor outlet temperature in said coking unit is operated at:
at least 470° C. for a drying time of at least 5 hours, or
at least 450° C. for a drying time of at least 6 hrs
by passage of a superheated vapor stream through the filled coke drum.

18. The processes of claim 1, wherein said anode grade green coke has the following properties: nickel less than about 175 ppm; vanadium less than about 250 ppm; sulfur less than about 35,000 ppmw; Hardgrove Grindability Index of less than about 100 and Volatile Combustible Matter of less than about 12 wt %.

19. The processes of claim 1, wherein the coker is operated at a Coker Throughput Ratio, defined as the sum of the fresh coker feed rate plus the coker liquid recycle rate divided by the fresh coker feed rate on a liquid volumetric basis, of less than about 1.25/1.

20. A process for upgrading residuum hydrocarbon feedstocks, comprising:
contacting a residuum hydrocarbon and hydrogen with a hydroconversion catalyst in an residuum hydroconversion reactor system;
recovering an effluent from the residuum hydroconversion reactor system;
separating the effluent from the residuum hydroconversion reactor system to recover two or more hydrocarbon fractions including at least a vacuum residuum fraction and a heavy vacuum gas oil fraction;
combining at least a portion of the heavy vacuum gas oil fraction and at least a portion of the vacuum residuum fraction to form a mixed heavy hydrocarbon fraction;
feeding at least a portion of the mixed heavy hydrocarbon fraction to a coker;
operating the coker at conditions to produce anode grade green coke and distillate hydrocarbons;
recovering the distillate hydrocarbons from the coker;
fractionating the distillate hydrocarbons recovered from the coker to recover three or more hydrocarbon fractions including a light distillates fraction, a heavy coker gas oil fraction, and a coker recycle fraction,
wherein the coker is operated at:
a heater coil outlet temperature of at least 500° C.;
a pressure in the range from about 20 psig to about 35 psig; and
with a drying time after the coking cycle of at least 2 hours.

21. The process of claim 20, further comprising:
contacting the heavy coker gas oil fraction and hydrogen with a hydroconversion catalyst in a hydroconversion reactor to convert at least a portion of the heavy coker gas oil fraction to distillate fuel range hydrocarbons;
recovering an effluent from the hydroconversion reactor; and
fractionating the effluent to form two or more hydrocarbon fractions.

22. The process of claim 20, wherein the coker is a delayed coker.

23. The process of claim 20, wherein the residuum hydroconversion reactor system comprises an ebullated bed hydroconversion reactor system.

24. The process of claim 20, wherein the residuum hydroconversion reactor system comprises a slurry-phase hydrocracking process.

25. The process of claim 20, wherein the hydroconversion reactor comprises at least one of a fixed-bed vacuum gas oil (VGO) hydrocracking reactor system, a fluidized bed VGO hydrocracking reactor system.

26. The processes of claim 20, wherein the coker is operated at a Coker Throughput Ratio, defined as the sum of the fresh coker feed rate plus the coker liquid recycle rate divided by the fresh coker feed rate on a liquid volumetric basis, of less than about 1.25/1.

27. A process for upgrading residuum hydrocarbon feedstocks, comprising:
contacting a residuum hydrocarbon and hydrogen with a hydroconversion catalyst in an residuum hydroconversion reactor system;
recovering an effluent from the residuum hydroconversion reactor system;
separating the effluent from the residuum hydroconversion reactor system to recover two or more hydrocarbon fractions including at least a vacuum residuum fraction and a heavy vacuum gas oil fraction;
combining at least a portion of the heavy vacuum gas oil fraction and at least a portion of the vacuum residuum fraction to form a mixed heavy hydrocarbon fraction;
feeding at least a portion of the mixed heavy hydrocarbon fraction to a coker;
operating the coker at conditions to produce anode grade green coke and distillate hydrocarbons;

recovering the distillate hydrocarbons from the coker;
fractionating the distillate hydrocarbons recovered from the coker to recover three or more hydrocarbon fractions including a light distillates fraction, a heavy coker gas oil fraction, and a coker recycle fraction,
wherein the coke drum vapor outlet temperature in said coking unit is operated at:
at least 470° C. for a drying time of at least 5 hours, or
at least 450° C. for a drying time of at least 6 hrs
by passage of a superheated vapor stream through the filled coke drum.

28. The process of claim 27, further comprising:
contacting the heavy coker gas oil fraction and hydrogen with a hydroconversion catalyst in a hydroconversion reactor to convert at least a portion of the heavy coker gas oil fraction to distillate fuel range hydrocarbons;
recovering an effluent from the hydroconversion reactor; and
fractionating the effluent to form two or more hydrocarbon fractions.

29. The process of claim 27, wherein the coker is a delayed coker.

30. The process of claim 27, wherein the residuum hydroconversion reactor system comprises an ebullated bed hydroconversion reactor system.

31. The process of claim 27, wherein the residuum hydroconversion reactor system comprises a slurry-phase hydrocracking process.

32. The process of claim 27, wherein the hydroconversion reactor comprises at least one of a fixed-bed vacuum gas oil (VGO) hydrocracking reactor system, a fluidized bed VGO hydrocracking reactor system.

33. The processes of claim 27, wherein the coker is operated at a Coker Throughput Ratio, defined as the sum of the fresh coker feed rate plus the coker liquid recycle rate divided by the fresh coker feed rate on a liquid volumetric basis, of less than about 1.25/1.

\* \* \* \* \*